US00PP17285P2

(12) United States Plant Patent
Keogh

(10) Patent No.: US PP17,285 P2
(45) Date of Patent: Dec. 19, 2006

(54) ***CUPHEA* PLANT NAMED 'FLAMENCO TANGO'**

(50) Latin Name: *Cuphea llavea×procumbens*
Varietal Denomination: FLAMENCO TANGO

(76) Inventor: Terry Keogh, 209 Bunker Road, Victoria Point, Queensland (AU), 4165

( * ) Notice: Subject to any disclaimer, the term of this patent is extended or adjusted under 35 U.S.C. 154(b) by 30 days.

(21) Appl. No.: 11/334,620

(22) Filed: Jan. 17, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new cultivar of *Cuphea* named 'FLAMENCO TANGO' that is characterized by dense upright habit, dark yellow-green foliage, and large pink flowers that bloom continuously throughout spring, summer and fall. In combination these traits set 'FLAMENCO TANGO' apart from all other existing varieties of *Cuphea* known to the inventor.

2 Drawing Sheets

Genus: *Cuphea.*
Species: *llavea×procumbens.*
Denomination: 'FLAMENCO TANGO'.

BACKGROUND OF THE INVENTION

The present invention relates to a new and distinct cultivar of *Cuphea* that is grown for use as an annual plant in container, or for use as a perennial plant for the landscape in frost-free regions. The new cultivar is known botanically as *Cuphea llavea×procumbens* and will be referred to hereinafter by the cultivar name 'FLAMENCO TANGO'.

The new *Cuphea* cultivar 'FLAMENCO TANGO' is a hybrid plant that resulted from the induced cross-pollination conducted by the inventor in June 2001 at the inventor's nursery in Brisbane, Queensland, Australia. 'FLAMENCO TANGO' was selected by the inventor in December 2003 based on flower shape, flower color and growth habit.

The inventor cross-pollinated an individual plant of the seed parent, *Cuphea llavea* 'Tiny Mice' (unpatented), and an individual plant of the pollen parent *Cuphea procumbens* (species, not a cultivar, unpatented). Observing that the resulting seedlings exhibited a range of flower colors and flower shapes, the inventor set aside several hundred of these seedlings for further growth trials in order to select the most promising combination of unique flower shape, flower color, and compactness of plant habit. Three, individual clones, from the seedling population were selected by the inventor in 2003. One selection constitutes the present invention, 'FLAMENCO TANGO'. The other two selections are the subjects of the inventors co-pending applications, 'FLAMENCO RUMBA' U.S. application Ser. No. 11/334,122 and 'FLAMENCO SAMBA' U.S. application Ser. No. 11/334,128.

'FLAMENCO TANGO' exhibits dense upright habit, large hairy flower buds, large pink flowers, and dark yellow-green foliage. Propagation is accomplished using softwood cuttings. The closest comparison plant known to the inventor is the inventor's co-pending variety *Cuphea* 'FLAMENCO RUMBA', which exhibits light red flowers and open, upright habit. 'FLAMENCO TANGO' is distinguishable from the comparison plant by pink flowers and dense, upright habit.

The new cultivar 'FLAMENCO TANGO' is distinguishable from the seed parent by flower color and number of flower lobes. The seed parent 'Tiny Mice' bears small orange flowers that individually exhibit two identical fused lobes, whereas 'FLAMENCO TANGO' exhibits pink flowers with six sub-equal lobes per individual flower. 'FLAMENCO TANGO' is distinguishable from the pollen parent by flower color and plant habit. *Cuphea procumbens* bears purple flowers and exhibits spreading habit, whereas 'FLAMENCO TANGO' exhibits pink flowers, and dense, upright habit.

The first asexual reproduction of 'FLAMENCO TANGO' was conducted by the inventor, in 2003 at the inventor's nursery in Brisbane, Australia. The method used for asexual propagation was vegetative cuttings. Since that time, the distinguishing characteristics of 'FLAMENCO TANGO' have been determined stable and have reproduced true to type in successive generations of asexual reproduction.

SUMMARY OF THE INVENTION

The following represent the distinguishing characteristics of the new *Cuphea* cultivar 'FLAMENCO TANGO'. In combination these traits set 'FLAMENCO TANGO' apart from all other existing varieties of *Cuphea* known to the inventor. 'FLAMENCO TANGO' has not been tested under all possible conditions and phenotypic differences may be observed with variations in environmental, climatic, and cultural conditions, however, without any variance in genotype.

1. *Cuphea llavea×procumbens* 'FLAMENCO TANGO' exhibits large pink flowers.
2. *Cuphea llavea×procumbens* 'FLAMENCO TANGO' blooms continuously throughout, spring, summer and fall.
3. *Cuphea llavea×procumbens* 'FLAMENCO TANGO' is an annual plant for container, or a perennial plant in frost-free regions.

4. *Cuphea llavea×procumbens* 'FLAMENCO TANGO' is readily propagated using vegetative cuttings.
5. *Cuphea llavea×procumbens* 'FLAMENCO TANGO' exhibits dense, upright habit.
6. *Cuphea llavea×procumbens* 'FLAMENCO TANGO' exhibits large hairy flower buds.
7. *Cuphea llavea×procumbens* 'FLAMENCO TANGO' is recommended for use in hanging basket, window box, clay container, and as a border plant in the landscape.
8. *Cuphea llavea×procumbens* 'FLAMENCO TANGO' exhibits dark yellow-green foliage.
9. *Cuphea llavea×procumbens* 'FLAMENCO TANGO' is hardy to USDA Zone 10.
10. *Cuphea llavea×procumbens* 'FLAMENCO TANGO' is 40 cm in height and 44 cm in width at maturity.

BRIEF DESCRIPTION OF THE DRAWINGS

The accompanying color drawings illustrate the overall appearance of the new *Cuphea* variety 'FLAMENCO TANGO' showing the colors as true as it is reasonably possible to obtain in colored reproductions of this type. Colors in the drawings may differ from the color values cited in the detailed botanical description, which accurately describe the actual colors of the new variety 'FLAMENCO TANGO'.

The drawing labeled

The drawing labeled

Figure 1:
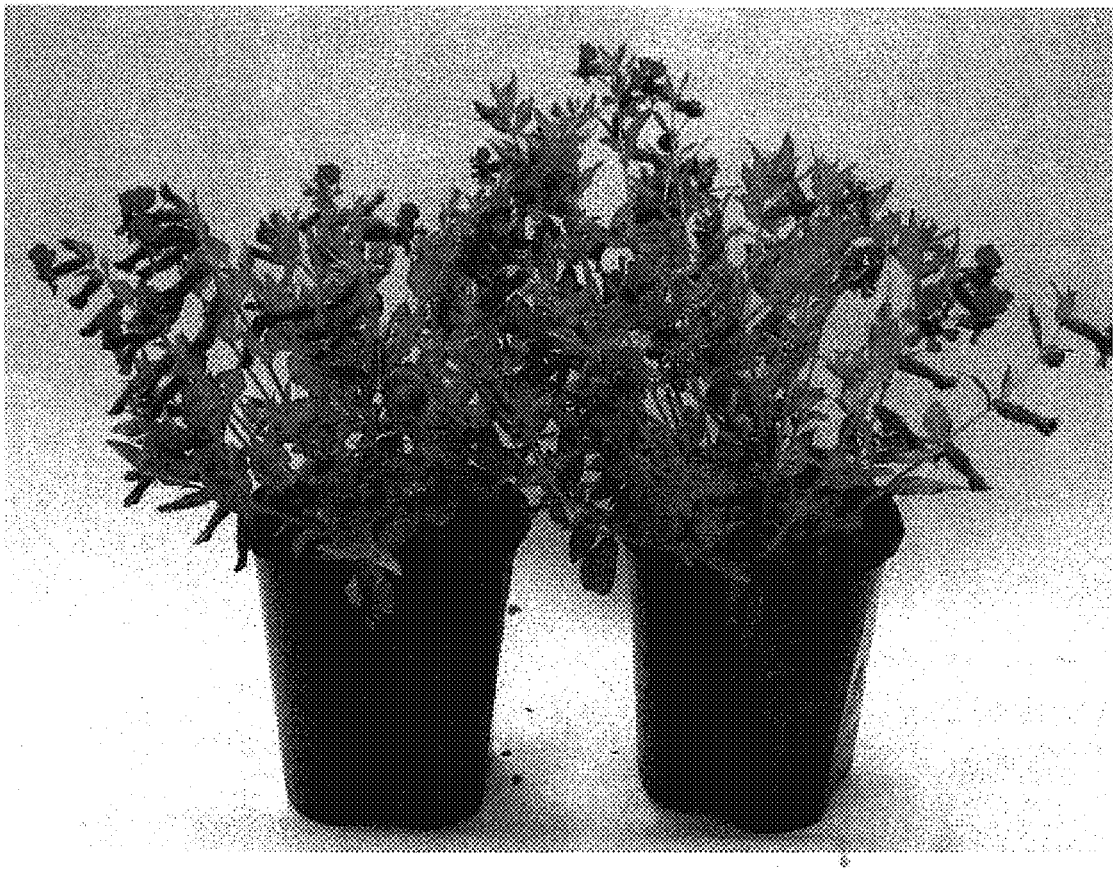
FIG. 1 depicts an entire plant in bloom from a side perspective.
Figure 2:
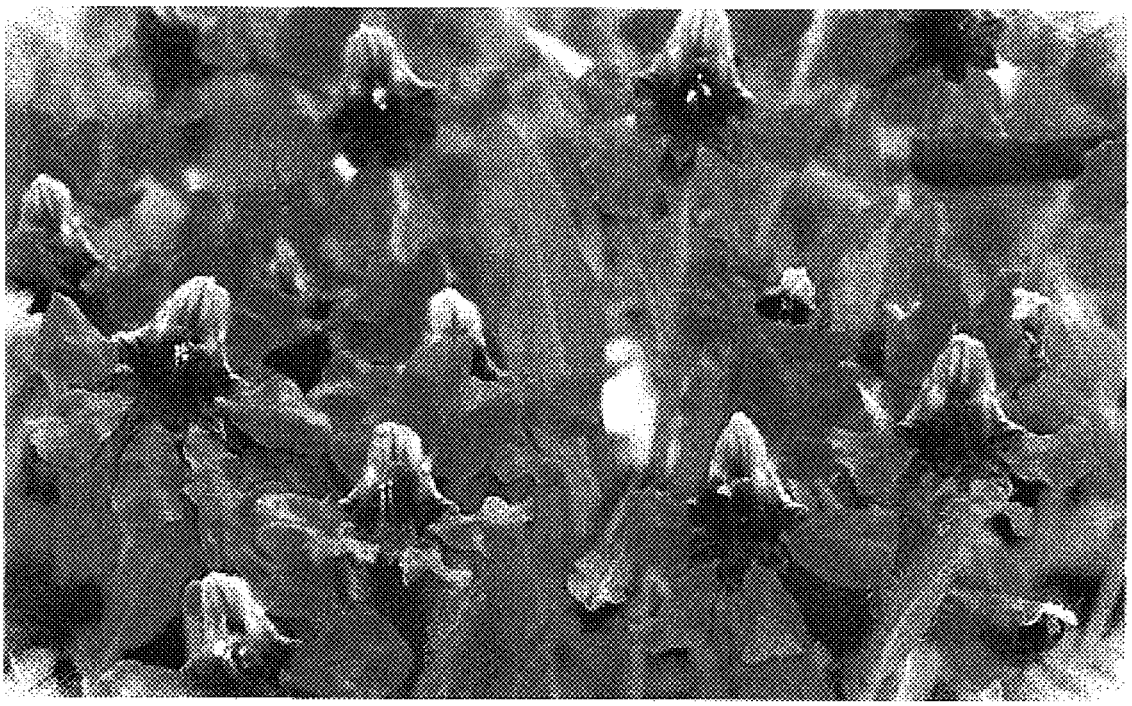
FIG. 2 depicts a close-up view of flower and bud.

All drawings are made using conventional techniques and although foliage colors may appear different from actual colors due to light reflectance, they are as accurate as possible by conventional photography.

BOTANICAL DESCRIPTION OF THE PLANT

The following is a detailed description of the *Cuphea* cultivar named 'FLAMENCO TANGO'. Data was collected and compiled in Arroyo Grande, Calif. from 2-liter container plants that were 12-months-old at the time. Color determinations are in accordance with the 2001 Royal Horticultural Society Colour Chart except where general color terms of ordinary dictionary significance are used. The growing requirements are similar to the species.

Botanical classification: *Cuphea llavea×procumbens* 'FLAMENCO TANGO'.
Genus: *Cuphea*.
Plant species: *llavea×procumbens*.
Denomination: FLAMENCO TANGO.
Common name: *Cuphea*.
Suggested uses: Recommended for use in hanging basket, window box, clay container, and as a border plant in the landscape.
Plant parentage: *Cuphea llavea×procumbens* 'FLAMENCO TANGO' is a hybrid plant that resulted from the induced cross-pollination of the following parent plants:
- *Seed parent.*—An individual *Cuphea llavea* 'Tiny Mice'.
- *Pollen parent.*—An individual *Cuphea procumbens*.

Plant type: An annual for use in containers and a perennial in frost-free regions.
Commercial category: Annual bedding plant; perennial in frost-free zones.
Recommended commercial container size: 2-liter commercial container.
Plant vigor: Moderate vigor.
Plant habit: Dense upright habit.
Plant dimensions (at maturity): 40 cm in height and 44 cm in width.
Plant dimensions (in a 2-liter container): 27 cm in height and 35 cm in width.
Plant hardiness: Hardy to USDA Zone 10.
Plant propagation: Readily propagated using vegetative cuttings.
Root system: Fleshy root system.
Cultural requirements: Plant in full sun using rich, well-draining potting soil, with regular watering.
Time to initiate rooting: 4–6 weeks are needed to produce roots on an initial cutting.
Crop time: 9–12 months are needed to produce a finished 2-liter container from a rooted cutting.
Seasonal interest: Large pink flowers that bloom continuously throughout spring, summer and fall.
Disease and pests: None known to the inventor.
Special growing considerations: Use a slow release fertilizer once a season and a water-soluble fertilizer twice a month.
Stem:
- *Basal trunk.*—One in number.
- *Basal trunk color.*—145A.
- *Basal trunk surface.*—Pubescent.
- *Basal trunk shape.*—Cylindrical.
- *Basal trunk diameter.*—0.50 cm.
- *Basal trunk height.*—1.50 cm.
- *Stem surface.*—Combination of pubescent and stipitate glandular.
- *Stem texture.*—Viscid.
- *Color of hairs.*—Individual colors 166B and 165D.
- *Stem shape.*—Cylindrical in shape.
- *Stem color.*—145A.
- *Stem diameter.*—3 mm.
- *Stem length.*—14 cm to 23 cm.
- *Branching pattern.*—Divergent.

Foliage:
- *Leaf type.*—Evergreen.
- *Internode length.*—Internode ranges from 1.50 cm to 2.50 cm in length.
- *Leaf arrangement.*—Opposite.
- *Leaf division.*—Simple.
- *Leaf quantity.*—18 to 20 leaves on an individual stem.
- *Leaf shape.*—Obovate.
- *Leaf base.*—Rounded.
- *Leaf apex.*—Apiculate.
- *Leaf venation pattern.*—Pinnate.
- *Vein color* (*abaxial and adaxial surfaces*).—147D.
- *Leaf surface* (*abaxial and adaxial*).—Sparsely hispid.
- *Leaf texture* (*abaxial and adaxial surfaces*).—Bristly.
- *Leaf attachment.*—Sessile and petiolate.
- *Petiole dimensions.*—4 mm in length and 1.75 mm in width.
- *Petiole shape.*—Cylindrical.
- *Petiole color.*—147A.
- *Petiole surface.*—Stipitate glandular.
- *Stipules.*—None observed.
- *Leaf margin.*—Minutely toothed leaf margin.
- *Leaf color* (*adaxial surface*).—147A.
- *Leaf color* (*abaxial surface*).—147B.
- *Leaf length.*—0.50 cm to 4.50 cm in length.
- *Leaf width.*—0.50 cm to 2 cm in width.
- *Foliar fragrance.*—None observed.

*Flower.*—Blooming seasons: Continuous blooming throughout spring, summer and fall. Inflorescence type: Raceme. Quantity of flowers: Quantity ranges from 4–8 flowers per raceme. Flower shape: Closest to salverform. Corolla: None observed. Hypanthium: Conspicuous. Flower aspect: Facing upward and outward. Flower color: 63B, N57A, 64B, 64C, 64A, and 138D all present on each flower. Flowers self-cleaning or persistent: Self-cleaning. Pedicel color: 146D. Pedicel shape: Cylindrical. Pedicel length: 2 mm. Pedicel diameter: 1.25 mm. Pedicel surface: Stipitate glandular. Flower bud shape: Cylindrical. Flower bud surface: Combination of stipitate glandular and multicostate. Flower bud texture: Viscid. Flower bud colors: N82A and 83A. Flower bud apex: Apex is closest to truncate, and enclosing 6 crumpled valvate lobes. Flower bud base: An individual bud base is a combination of gibbous and oblique. Flower bud dimensions: 2 cm in length and 0.50 cm in diameter. Flower diameter: 3 cm. Flower depth: 2.25 cm. Corolla tube diameter: 0.50 cm. Corolla tube length: 2 cm. Corolla tube color (ventral surface): 83A and 83C. Corolla tube color (dorsal surface): 138D and 64A. Corolla tube shape: Tubular. Corolla tube apex: Flared. Corolla tube base: Combination of gibbous and oblique. Corolla tube surface (ventral and dorsal surfaces): Combination of multicostate and stipitate glandular. Corolla tube texture: Viscid. Petals: Apetalous.

*Calyx* (*sepals form valvate lobes*).—Valvate lobe number: 6 sub-equal valvate lobes; 4 small lobes and 2 large lobes present on an individual flower. Valvate lobe attachment: Individual valvate lobes are attached at the summit of hypanthium. Valvate lobe arrangement: Rotate arrangement. Large valvate lobe dimensions: 1.25 cm in width and 1.25 cm in length. Small valvate lobe dimensions: 0.75 cm in width and 1 cm in length. Valvate lobe color (adaxial and abaxial surfaces): Colors 64B and 64C. Valvate lobe texture: Delicate. Valvate lobe surfaces (adaxial and abaxial): Rugose. Valvate lobe appearance (adaxial and abaxial surfaces): Irridescent. Valvate lobe shape: Orbicular and rotund shaped lobes. Valvate lobe apex: Obtuse and rounded. Valvate lobe base: Cuneate and rotund lobe base. Valvate lobe margin: Sinuous. Valvate lobes unfused or fused: Unfused.

*Flower fragrance.*—Slight sweet scent.

*Reproductive organs.*—Stamens: Stamens are 10 in number semi-exserted and adnate to the ventral surface of an individual corolla tube. Color of stamens: 77D. Stamen dimensions: On an individual flower, 5 stamens are 0.75 mm in length and 5 stamens are 1.25 mm in length. Anthers: On an individual flower the 5 long stamens are tufted with dense violet hairs and the 5 short stamens exhibit anthers. Color of hairs: 83B. Anther dimensions: 0.75 mm in length and 0.75 mm in width. Anther color: 150D. Amount of pollen: Minimal amount. Pollen color: 150D. Pistil: One in number. Pistil length: 1.25 cm. Pistil shape: Filament. Pistil surface: Pubescent. Pistil color: Individual colors 145C and 77B. Stigma color: 77B. Stigma shape: Bifid. Stigma dimensions: 0.25 mm in length and 0.25 mm in diameter. Ovary position: Superior. Ovary shape: Globose. Ovary color: 138D. Ovary surface: Rugose. Ovary dimensions: 0.75 cm in height and 0.75 cm in diameter.

*Fruit.*—Dry, dehiscent, ovoid capsule.

*Capsule.*—3 locules, splitting between each.

*Color* (*prior to splitting*).—Between 152A and 152D.

*Dimensions* (*prior to splitting*).—6 mm in diameter.

*Seed.*—Number of seeds: Approximately 25. Seed surface: Glabrous. Seed Shape: Globose. Seed color: 138D. Seed dimensions: 0.50 mm in diameter.

I claim:

1. A new and distinct variety of *Cuphea* plant named 'FLAMENCO TANGO' as described and illustrated herein.

* * * * *